US011160463B2

(12) United States Patent
Naude

(10) Patent No.: US 11,160,463 B2
(45) Date of Patent: Nov. 2, 2021

(54) MULTI-SENSOR INTERACTIVE PATIENT CARE POD

(71) Applicant: Eddie Naude, Kelowna (CA)

(72) Inventor: Eddie Naude, Kelowna (CA)

(*) Notice: Subject to any disclaimer, the term of this patent is extended or adjusted under 35 U.S.C. 154(b) by 229 days.

(21) Appl. No.: 16/691,020

(22) Filed: Nov. 21, 2019

(65) Prior Publication Data

US 2021/0153753 A1 May 27, 2021

(51) Int. Cl.
| | |
|---|---|
| *A61B 5/0205* | (2006.01) |
| *A61B 5/1455* | (2006.01) |
| *A61B 5/01* | (2006.01) |
| *A61B 5/145* | (2006.01) |
| *A61B 5/00* | (2006.01) |
| *A61N 5/06* | (2006.01) |

(Continued)

(52) U.S. Cl.
CPC ........ *A61B 5/02055* (2013.01); *A61B 5/0022* (2013.01); *A61B 5/0077* (2013.01); *A61B 5/01* (2013.01); *A61B 5/14542* (2013.01); *A61B 5/14552* (2013.01); *A61B 5/7405* (2013.01); *A61B 5/7445* (2013.01); *A61B 5/7475* (2013.01); *A61N 5/06* (2013.01); *A61B 5/021* (2013.01); *A61B 5/0816* (2013.01); *A61N 2005/0663* (2013.01); *B60R 16/037* (2013.01); *G05D 1/021* (2013.01)

(58) Field of Classification Search
CPC .... A61B 2560/0406; A61B 2560/0462; A61B 5/0022; A61B 5/0077; A61B 5/01; A61B 5/0205; A61B 5/02055; A61B 5/021; A61B 5/0816; A61B 5/14542; A61B 5/14552; A61B 5/6888; A61B 5/6891; A61B 5/70; A61B 5/7405; A61B 5/7445; A61B 5/7465; A61B 5/7475; A61B 5/749; A61N 2005/064; A61N 2005/0662; A61N 2005/0663; A61N 5/06; B60R 16/037; G05D 1/021

See application file for complete search history.

(56) References Cited

U.S. PATENT DOCUMENTS

| | | | |
|---|---|---|---|
| 9,152,769 B2 * | 10/2015 | Baudino | A61B 5/6888 |
| 2009/0137882 A1 * | 5/2009 | Baudino | G16H 50/80 |
| | | | 600/301 |

FOREIGN PATENT DOCUMENTS

WO    WO 2017145177 A1 * 8/2017

* cited by examiner

*Primary Examiner* — Jonathan T Kuo
(74) *Attorney, Agent, or Firm* — Pharar Patents & Intellectual Property; Andrew A. Pharar

(57) ABSTRACT

A multi-sensor interactive patient care pod is disclosed herein. In one embodiment the system may comprise a telemedicine pod having a plurality of physiological sensors and an integrated computing device allowing medical practitioners to remotely gather increased patient information and provide advanced levels of healthcare and service. The system may have sensors for measuring body weight, heart rate, body temperature, blood pressure, breathing rate, oxygen saturation, and any other appropriate parameters. The multi-sensor interactive patient care pod may comprise an enclosed pod in a first orientation, and may open by the combined sliding of its front cowling and lifting of its top cowling to allow patient ingress and egress. The system may further comprise a mobile device that can be placed in any appropriate location, and may further integrate smart technologies such as machine learning, voice and face recognition, self-cleaning, self-driving, and self-locking technologies.

20 Claims, 18 Drawing Sheets

(51) Int. Cl.
*G05D 1/02* (2020.01)
*A61B 5/021* (2006.01)
*A61B 5/08* (2006.01)
*B60R 16/037* (2006.01)

MULTI-SENSOR INTERACTIVE PATIENT CARE POD

TECHNICAL FIELD OF THE INVENTION

The present invention relates in general to medical devices, and, more specifically, to a multi-sensor interactive patient care pod.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Medicine, or the practice of medicine, refers generally to the caring for patients in some healthcare setting. Such caring for patients may include preventative and restorative medical practices, and can encompass systems including allopathic and homeopathic methods for treating diseases and pathologies. The practice of medicine is often performed in a hospital or clinical office setting, though can also be performed at such varied sites as nursing homes, within the patient's own home, or even at other public locations like pharmacies, and various types of medicinal practices may be performed by licensed professionals or by learned individuals.

Telemedicine is the art of practicing medicine remotely, usually via wired or wireless communication, and allows medical practitioners to assist patients without being in the same location as the patient. Physicians, physician assistants, nurses, and others are now able to share and exchange information with a patient in real time, and in a Health Insurance Portability and Accountability Act (HIPAA) compliant manner. Such interactions can be done over the phone or via the internet from specialized locations or even from the patient's own home.

Specialized locations for providing telemedicine often comprise a computing system having a visual display and some input and output devices. A patient is able to sit at the location and consult with a medical practitioner using the computing system, and the medical practitioner can perform a basic physical examination or follow-up examination and deliver appropriate continuation of care. Such locations are often limited in their abilities to conduct a thorough examination of the patient, though, and cannot provide the advanced level of analysis and care advantageous in the practice of medicine today.

Thus, there is a need in the art for a multi-sensor interactive patient care pod that can perform advanced patient analysis allowing a medical practitioner to deliver a level of patient care advantageous in the practice of medicine. It is to these ends that the present invention has been developed.

BRIEF SUMMARY OF THE INVENTION

To minimize the limitations in the prior art, and to minimize other limitations that will be apparent upon reading and understanding the present specification, the present invention describes a multi-sensor interactive patient care pod.

It is an objective of the present invention to provide a multi-sensor interactive patient care pod that may comprise a telemedicine device.

It is another objective of the present invention to provide a multi-sensor interactive patient care pod that may comprise a telemedicine pod.

It is another objective of the present invention to provide a multi-sensor interactive patient care pod that may comprise a structural framework.

It is another objective of the present invention to provide a multi-sensor interactive patient care pod that may comprise a rear cowling.

It is another objective of the present invention to provide a multi-sensor interactive patient care pod that may comprise a sliding front cowling.

It is another objective of the present invention to provide a multi-sensor interactive patient care pod that may comprise a track.

It is another objective of the present invention to provide a multi-sensor interactive patient care pod that may comprise a sled.

It is another objective of the present invention to provide a multi-sensor interactive patient care pod that may comprise a lifting top cowling.

It is another objective of the present invention to provide a multi-sensor interactive patient care pod that may comprise a plurality of cowling arms.

It is another objective of the present invention to provide a multi-sensor interactive patient care pod that may comprise a plurality of cowling supports.

It is another objective of the present invention to provide a multi-sensor interactive patient care pod that may comprise a multi-sensor seat.

It is another objective of the present invention to provide a multi-sensor interactive patient care pod that may comprise a plurality of physiological sensors.

It is another objective of the present invention to provide a multi-sensor interactive patient care pod that may comprise a body weight sensor.

It is another objective of the present invention to provide a multi-sensor interactive patient care pod that may comprise a pulse oximetry sensor.

It is another objective of the present invention to provide a multi-sensor interactive patient care pod that may comprise a body temperature sensor.

It is another objective of the present invention to provide a multi-sensor interactive patient care pod that may comprise a blood pressure sensor.

It is another objective of the present invention to provide a multi-sensor interactive patient care pod that may comprise a breathing rate sensor.

It is another objective of the present invention to provide a multi-sensor interactive patient care pod that may comprise an oxygen saturation sensor.

It is another objective of the present invention to provide a multi-sensor interactive patient care pod that may comprise a computing device.

It is another objective of the present invention to provide a multi-sensor interactive patient care pod that may comprise an electronic interface.

It is another objective of the present invention to provide a multi-sensor interactive patient care pod that may comprise a display device.

It is another objective of the present invention to provide a multi-sensor interactive patient care pod that may comprise a manual input device.

It is another objective of the present invention to provide a multi-sensor interactive patient care pod that may comprise voice recognition technology.

It is another objective of the present invention to provide a multi-sensor interactive patient care pod that may comprise wireless connectivity.

It is another objective of the present invention to provide a multi-sensor interactive patient care pod that may comprise a proprietary software application.

It is another objective of the present invention to provide a multi-sensor interactive patient care pod that may comprise a resilient material of construction.

It is another objective of the present invention to provide a multi-sensor interactive patient care pod that may comprise an antimicrobial layer.

It is another objective of the present invention to provide a multi-sensor interactive patient care pod that may comprise an antimicrobial material of construction.

It is another objective of the present invention to provide a multi-sensor interactive patient care pod that may comprise a mobile device.

It is another objective of the present invention to provide a multi-sensor interactive patient care pod that may comprise a wheeled device.

It is another objective of the present invention to provide a multi-sensor interactive patient care pod that may comprise a self-driving device.

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

DETAILED DESCRIPTION OF THE INVENTION

Figure 1:
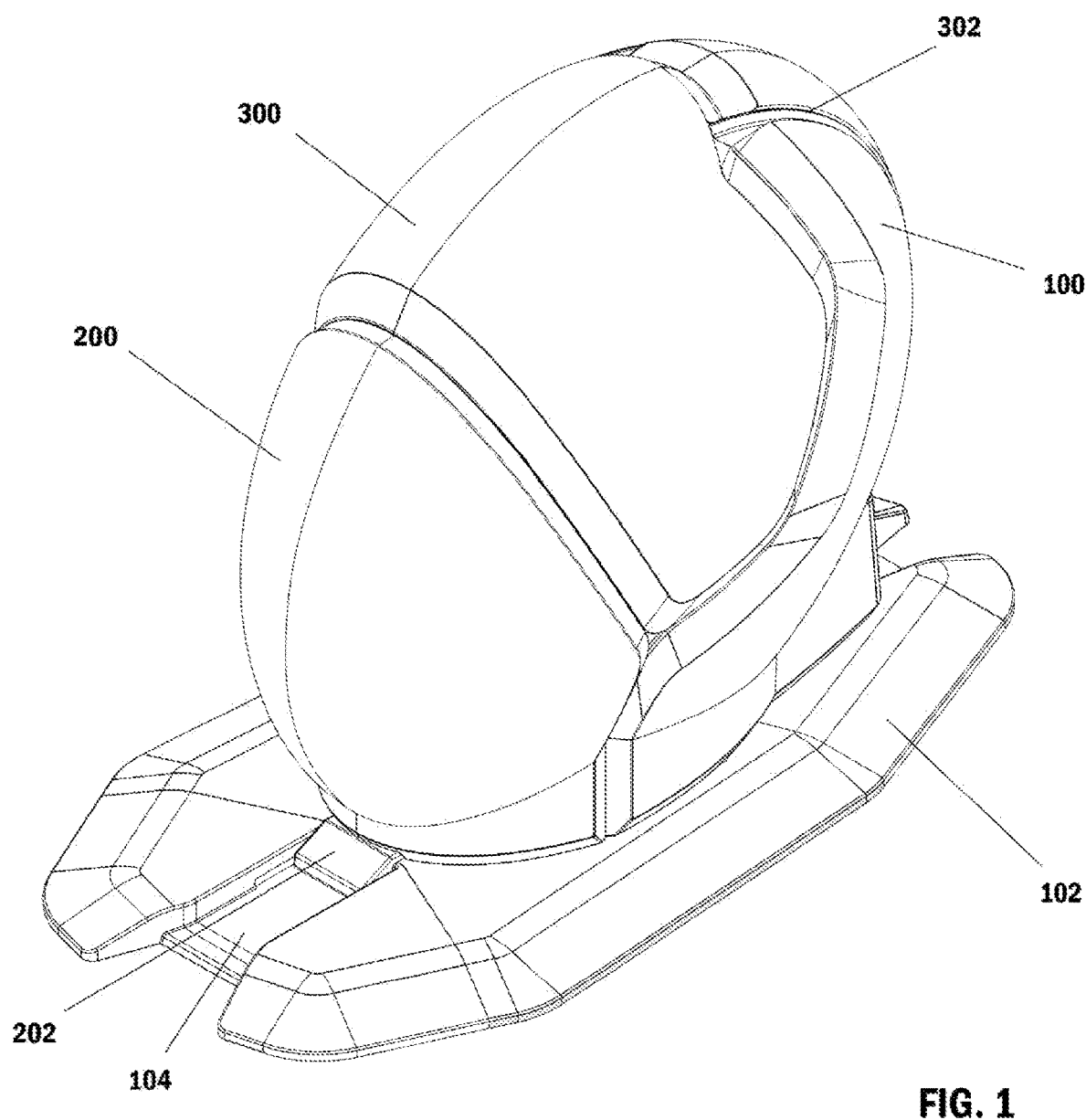
FIG. 1 illustrates a front isometric perspective view of a multi-sensor interactive patient care pod in a closed orientation, as contemplated by the present disclosure.
Figure 2:
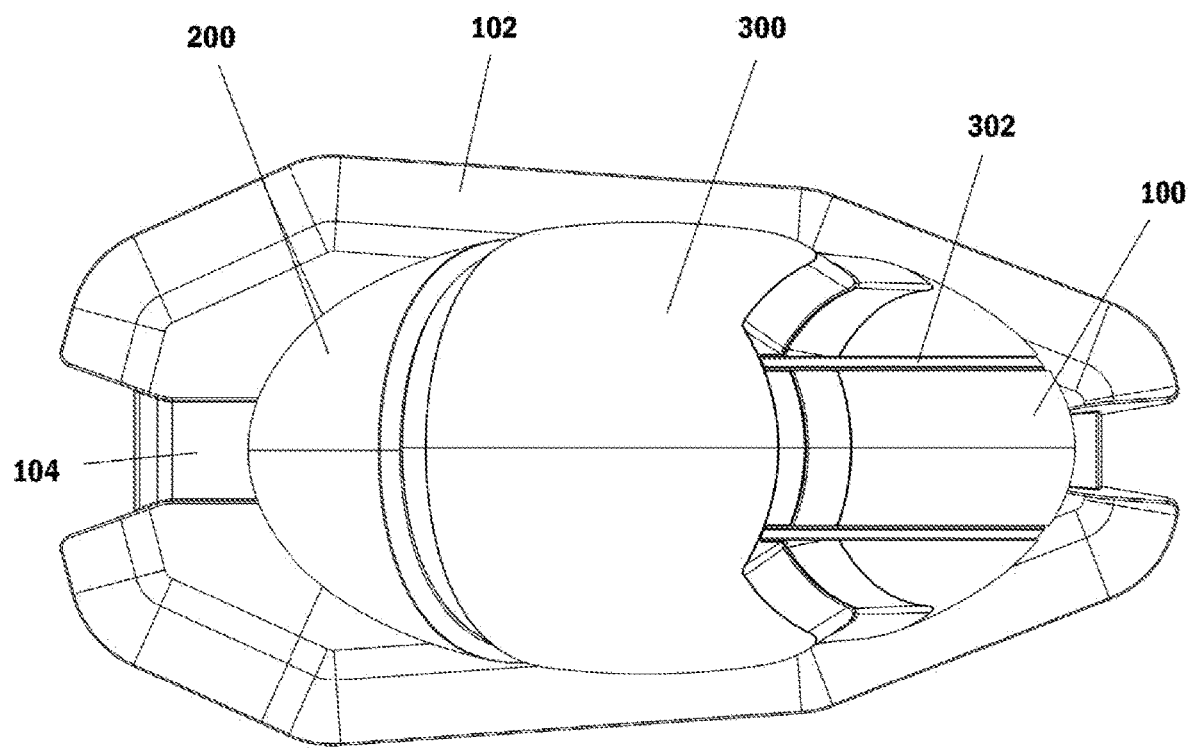
FIG. 2 illustrates a top plan view of a multi-sensor interactive patient care pod in a closed orientation, as contemplated by the present disclosure.
Figure 3:
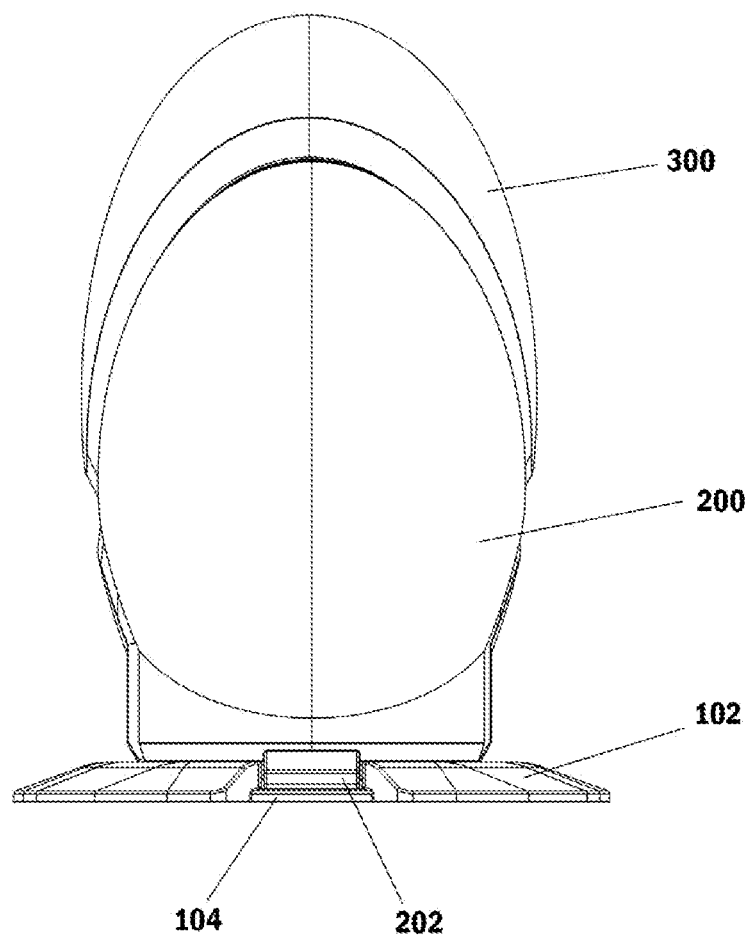
FIG. 3 illustrates a front elevation view of a multi-sensor interactive patient care pod in a closed orientation, as contemplated by the present disclosure.
Figure 4:
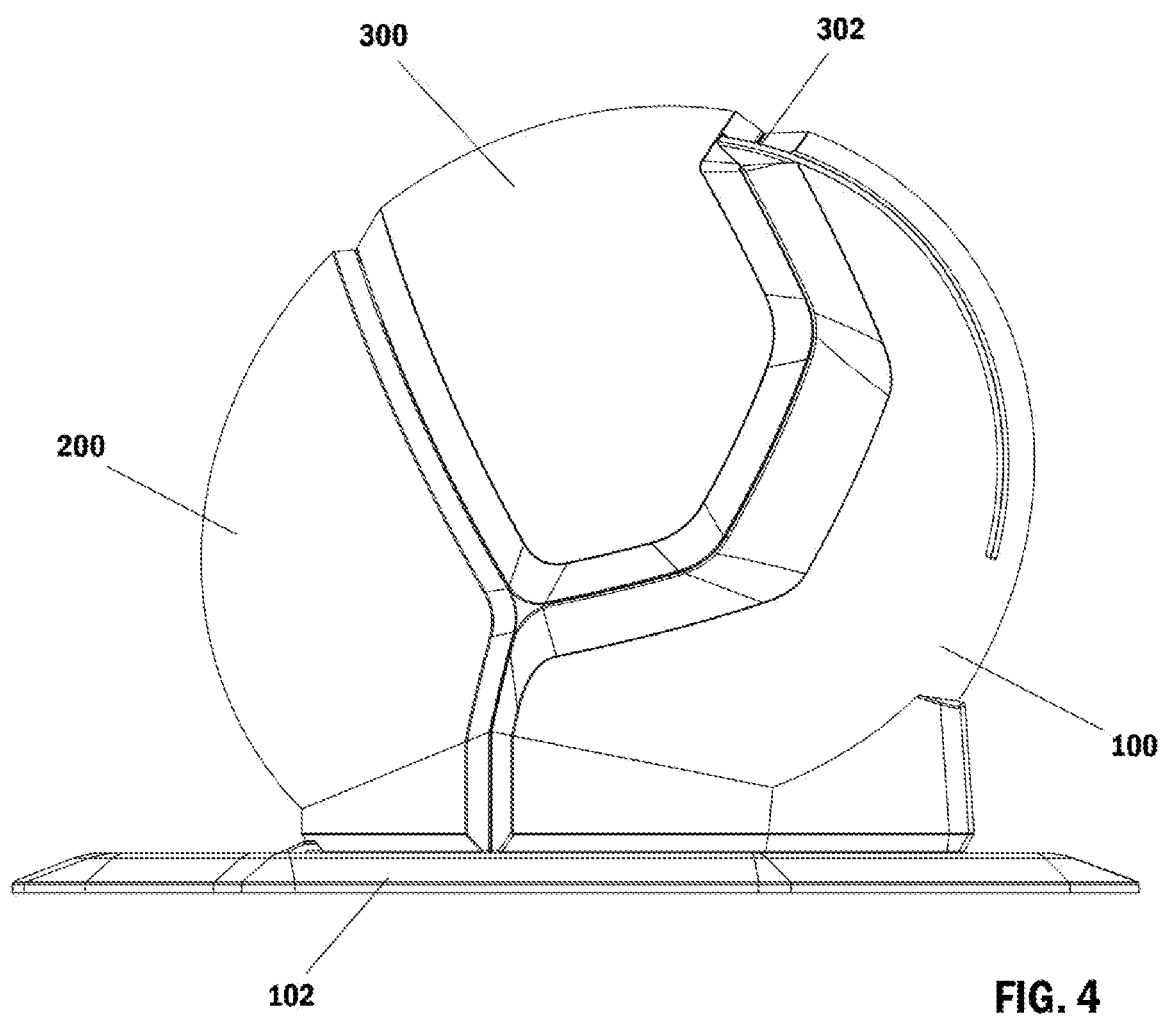
FIG. 4 illustrates a left side elevation view of a multi-sensor interactive patient care pod in a closed orientation, as contemplated by the present disclosure.
Figure 5:
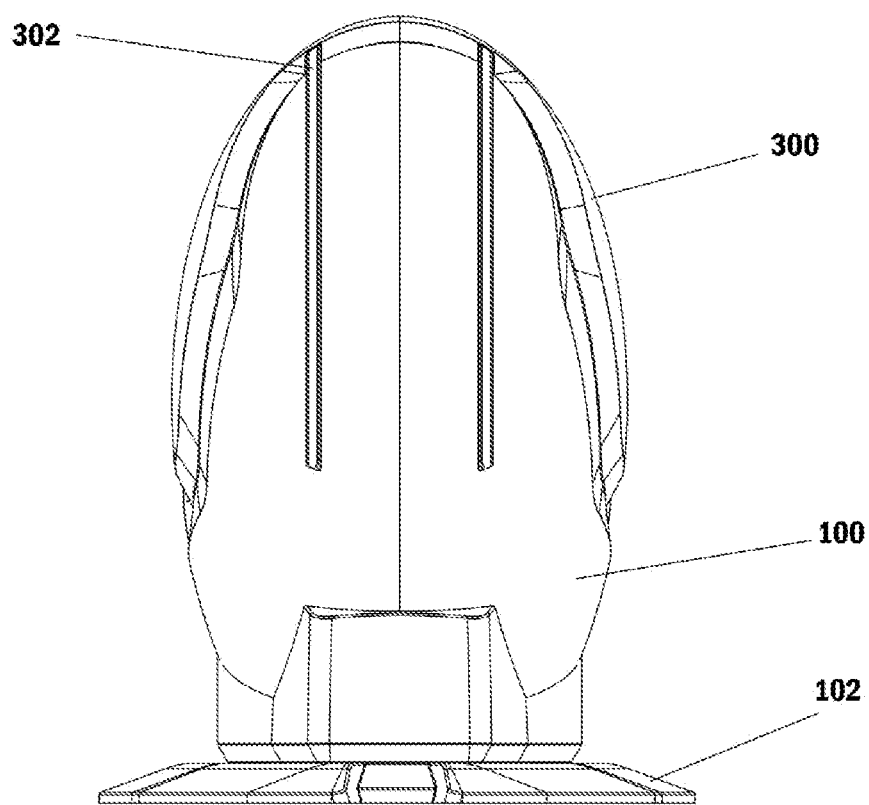
FIG. 5 illustrates a rear elevation view of a multi-sensor interactive patient care pod in a closed orientation, as contemplated by the present disclosure.
Figure 6:
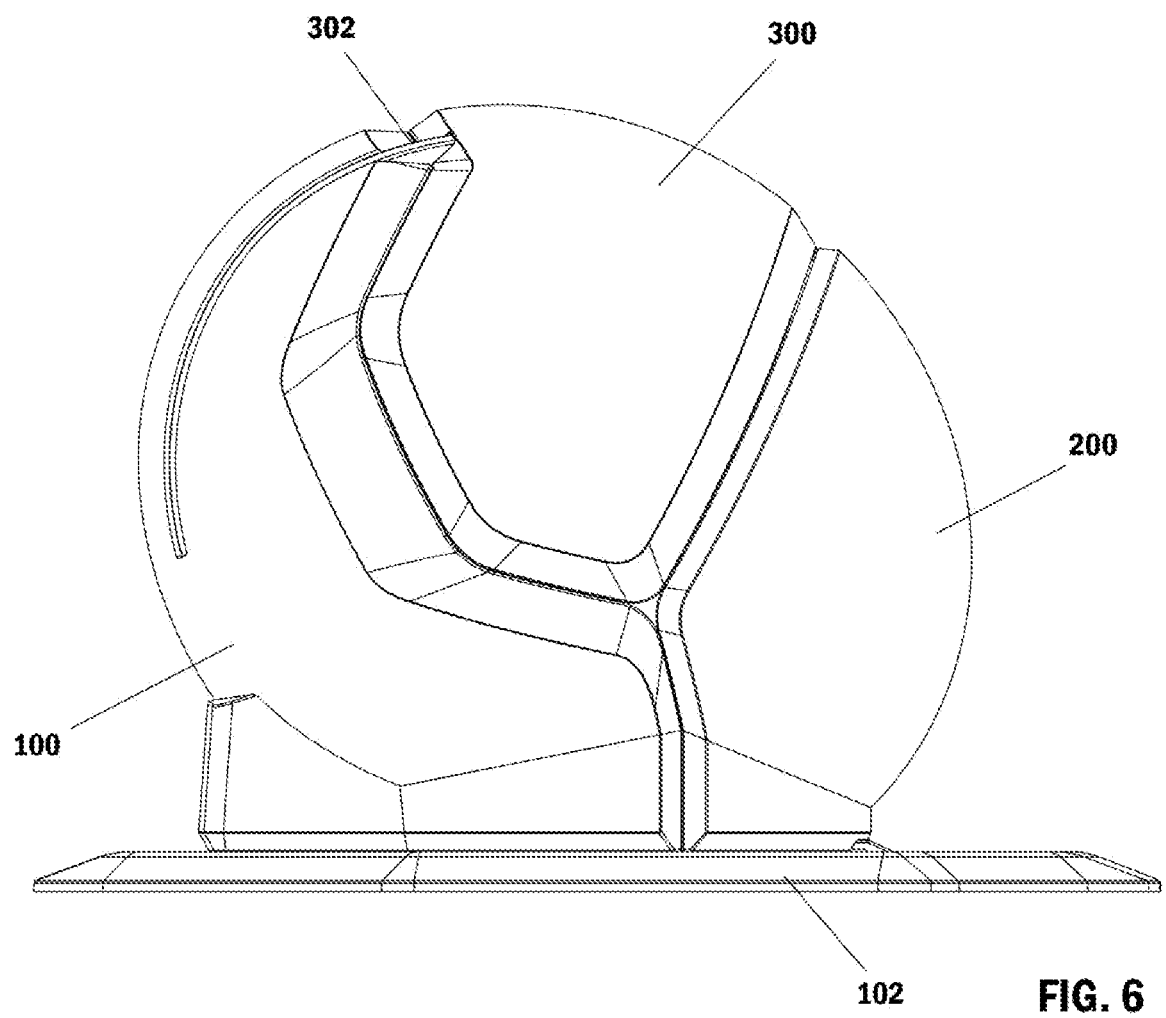
FIG. 6 illustrates a right side elevation view of a multi-sensor interactive patient care pod in a closed orientation, as contemplated by the present disclosure.
Figure 7:
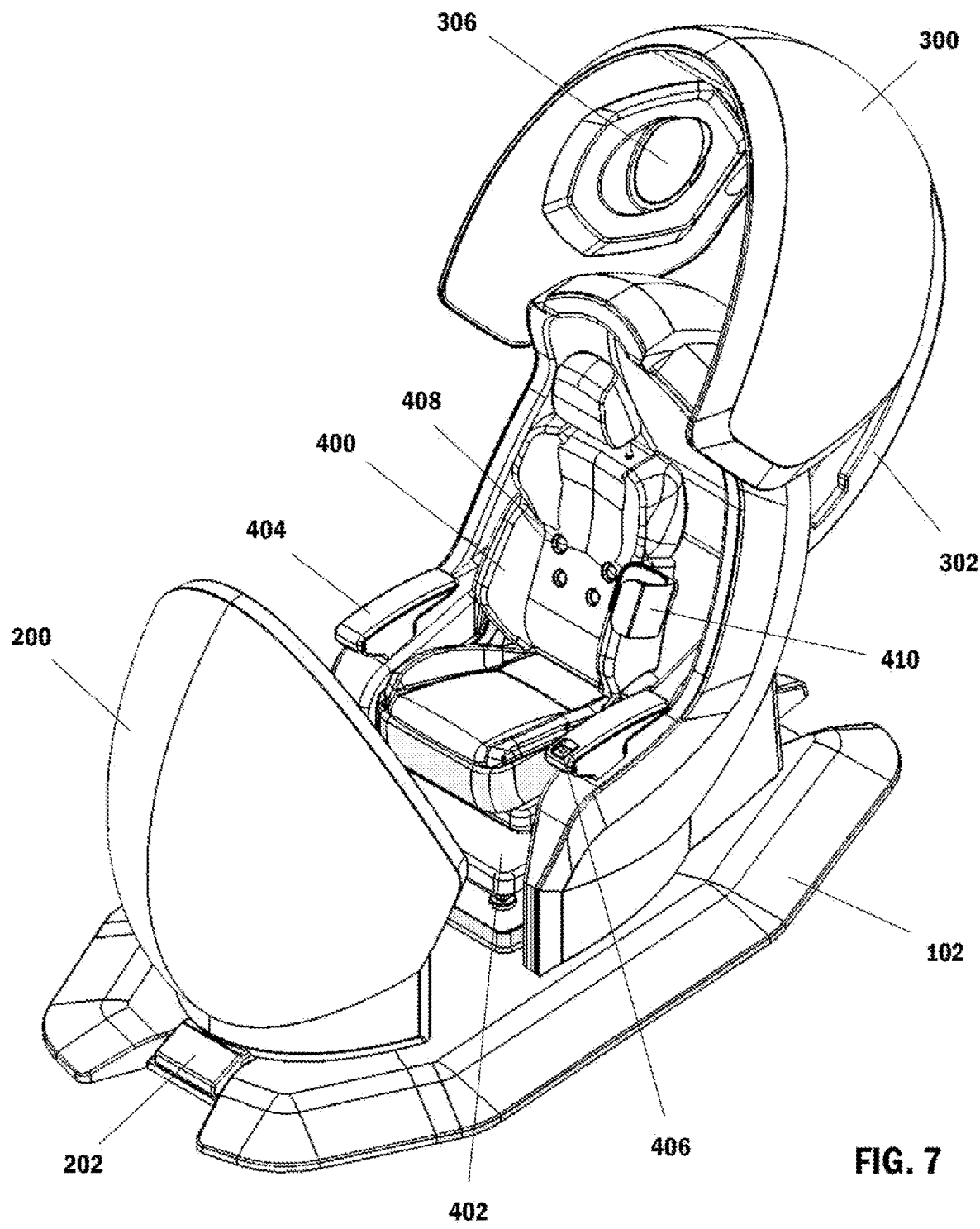
FIG. 7 illustrates a front isometric perspective view of a multi-sensor interactive patient care pod in an open orientation, as contemplated by the present disclosure.
Figure 8:
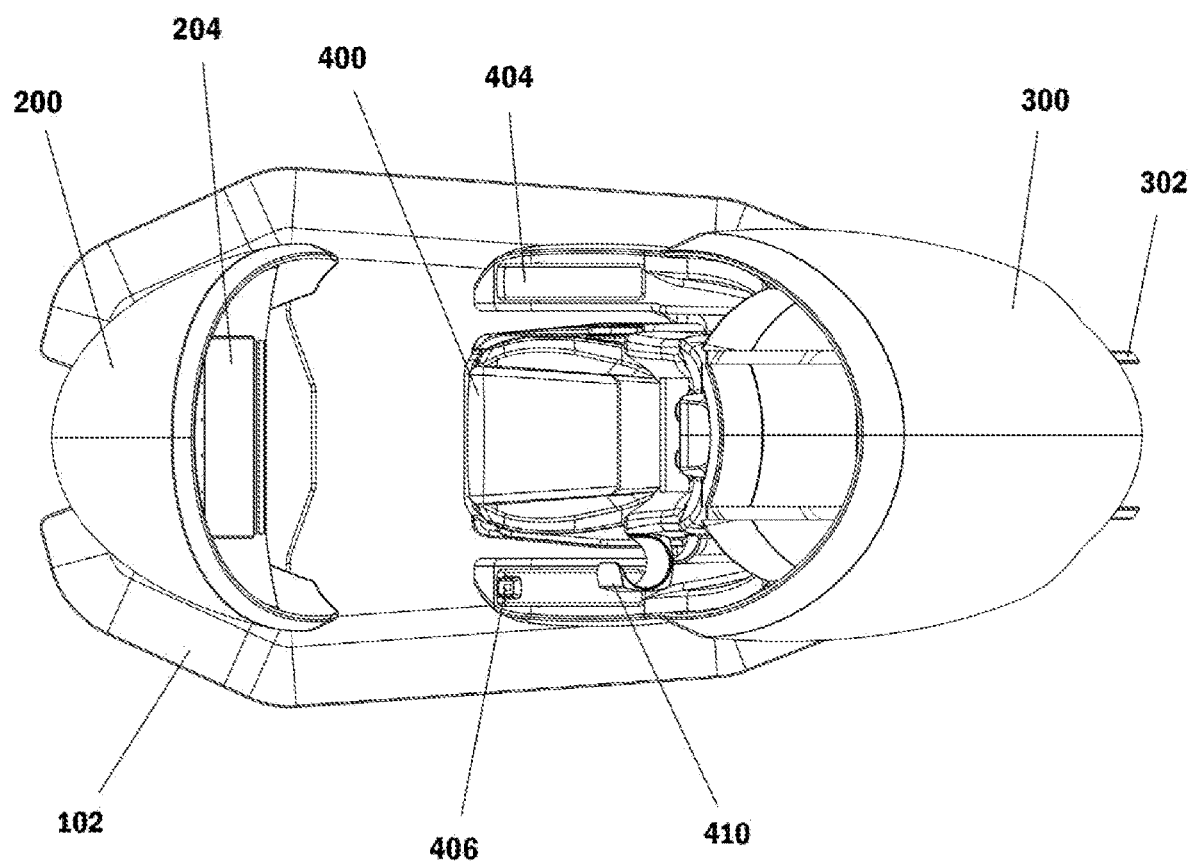
FIG. 8 illustrates a top plan view of a multi-sensor interactive patient care pod in an open orientation, as contemplated by the present disclosure.
Figure 9:
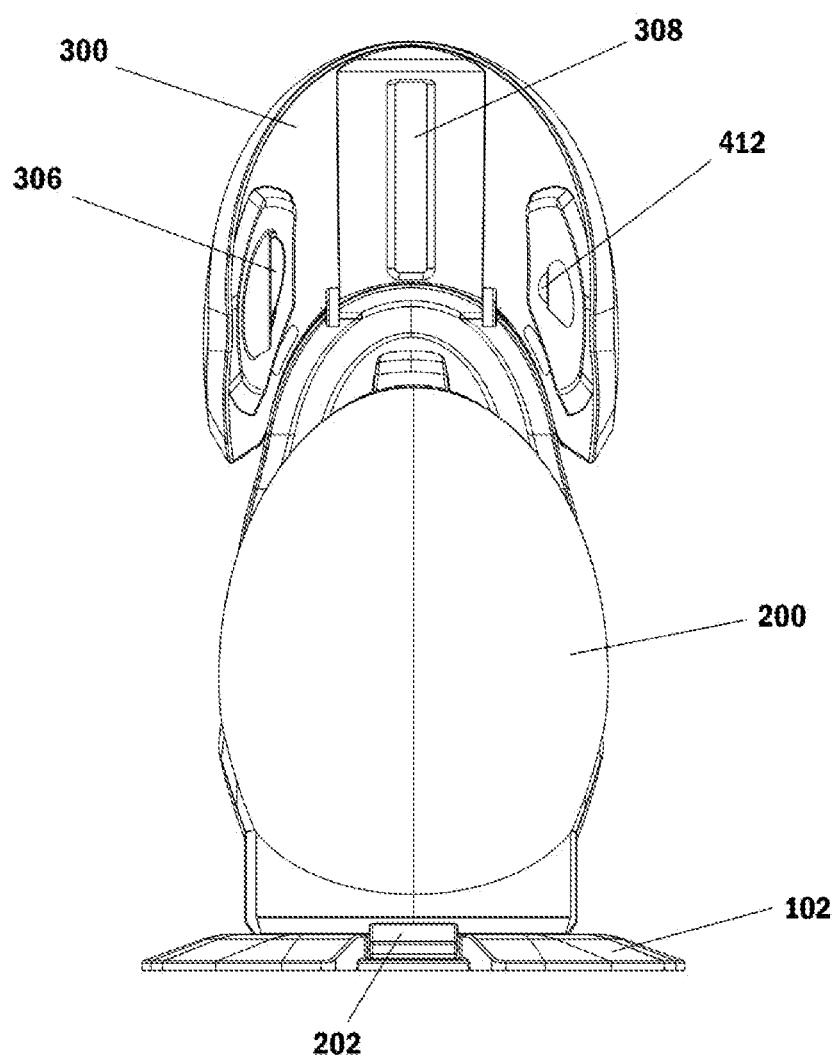
FIG. 9 illustrates a front elevation view of a multi-sensor interactive patient care pod in an open orientation, as contemplated by the present disclosure.
Figure 10:
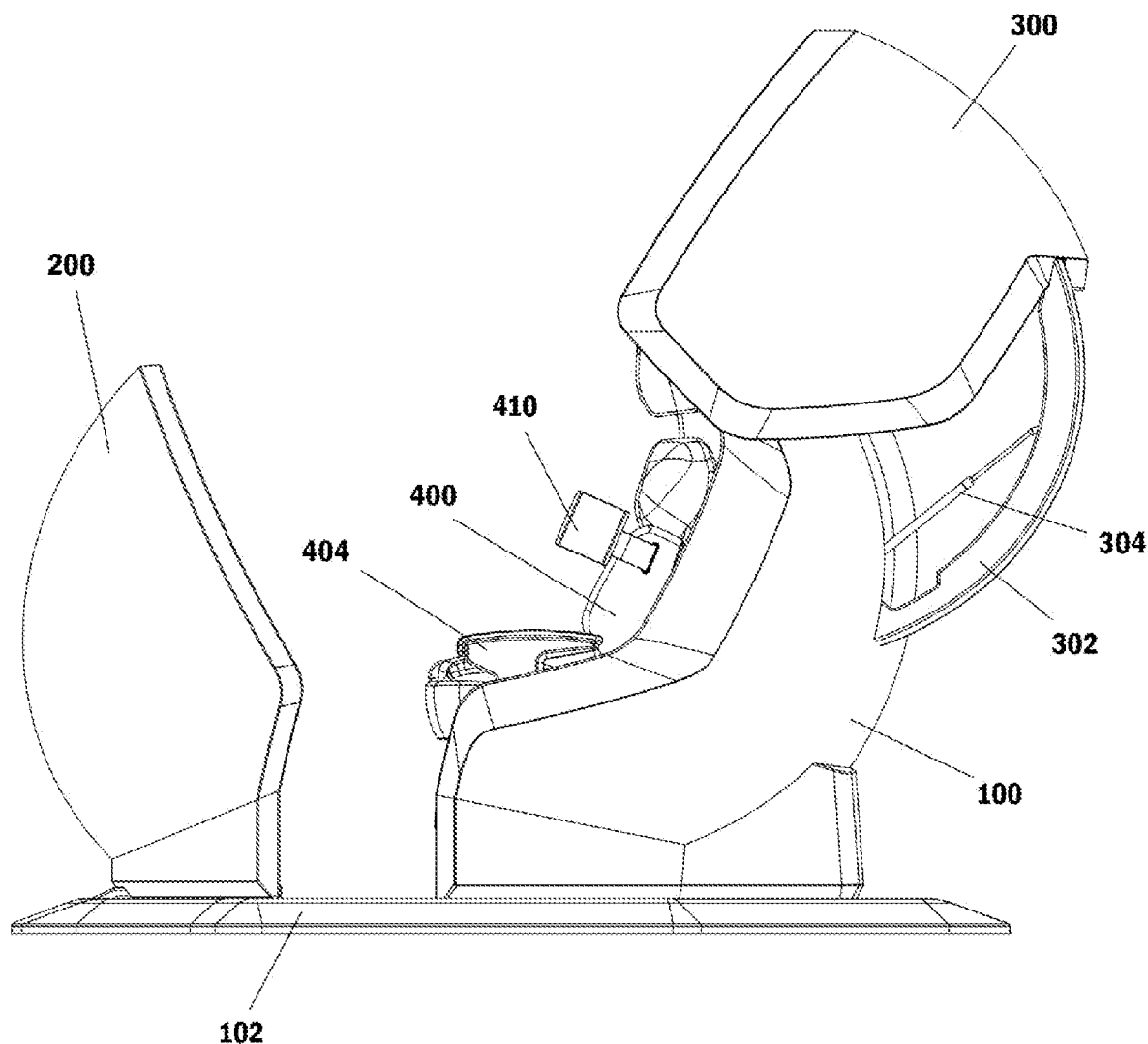
FIG. 10 illustrates a left side elevation view of a multi-sensor interactive patient care pod in an open orientation, as contemplated by the present disclosure.
Figure 11:
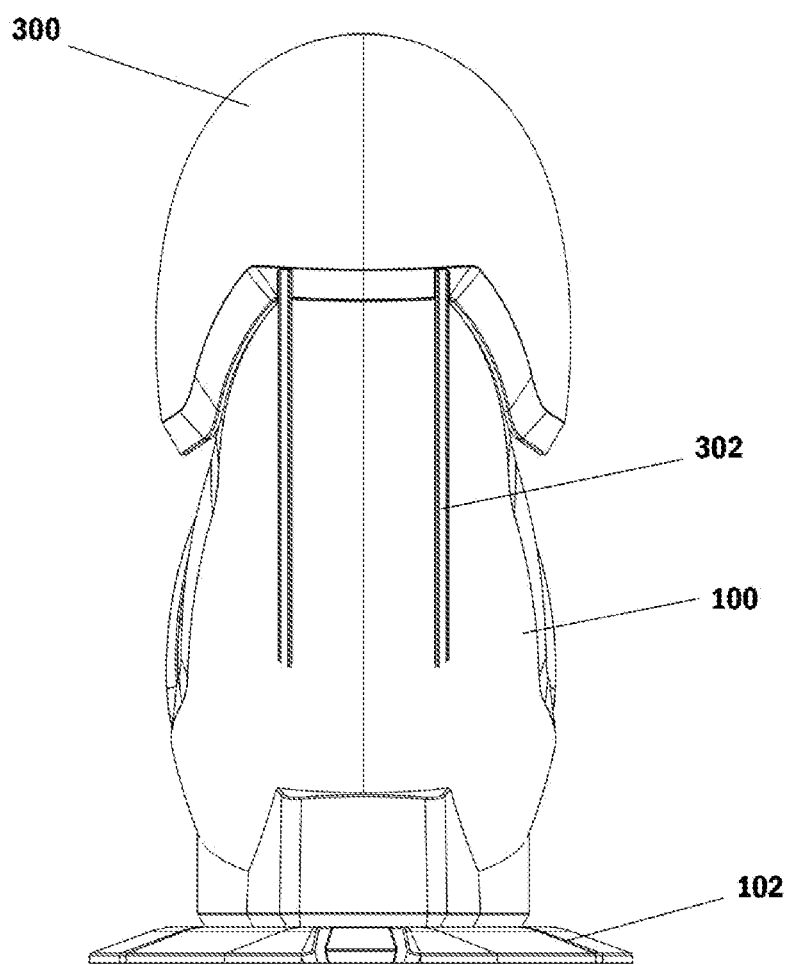
FIG. 11 illustrates a rear elevation view of a multi-sensor interactive patient care pod in an open orientation, as contemplated by the present disclosure.
Figure 12:
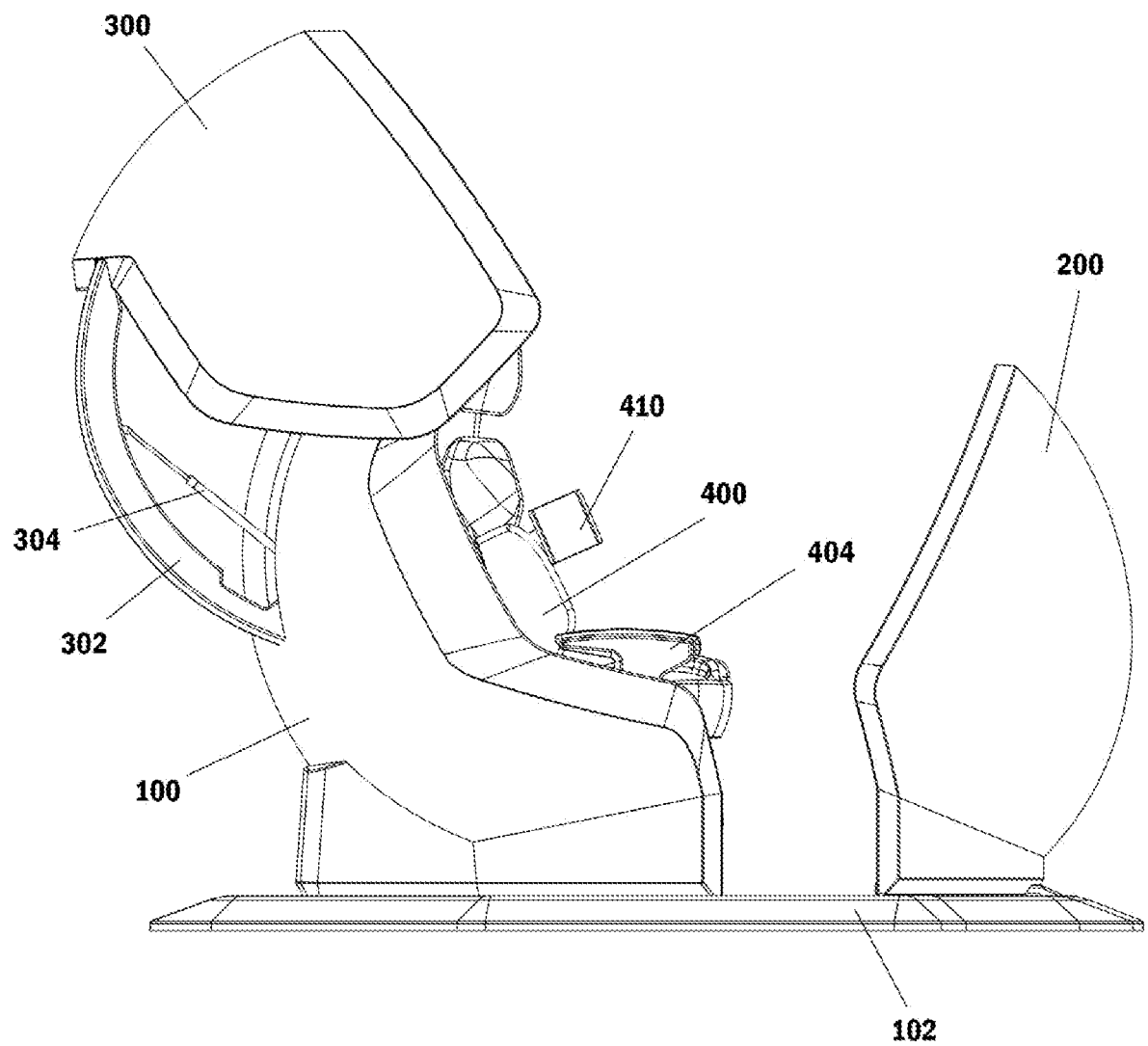
FIG. 12 illustrates a right side elevation view of a multi-sensor interactive patient care pod in an open orientation, as contemplated by the present disclosure.
Figure 13:
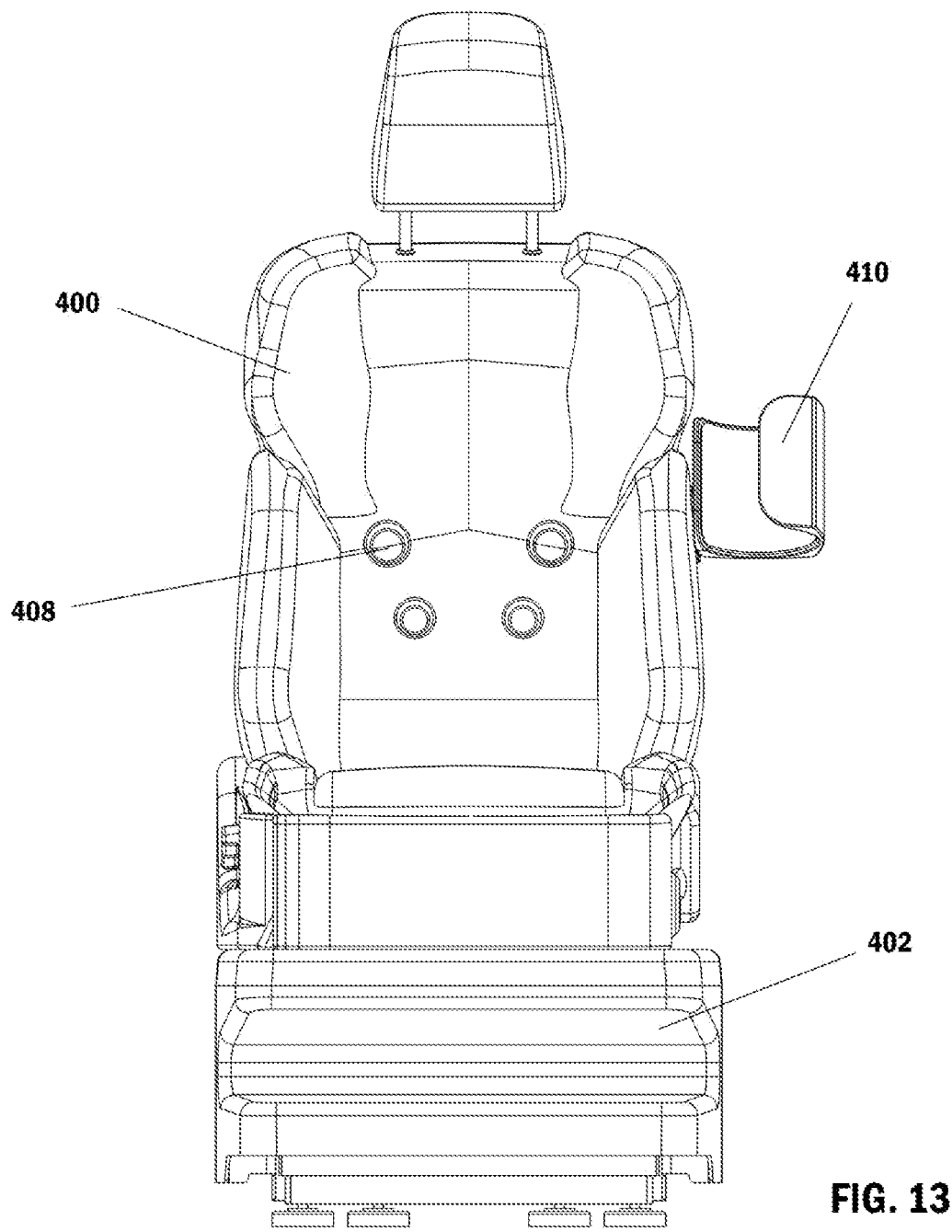
FIG. 13 illustrates a front elevation view of a multi-sensor seat of a multi-sensor interactive patient care pod, as contemplated by the present disclosure.
Figure 14:
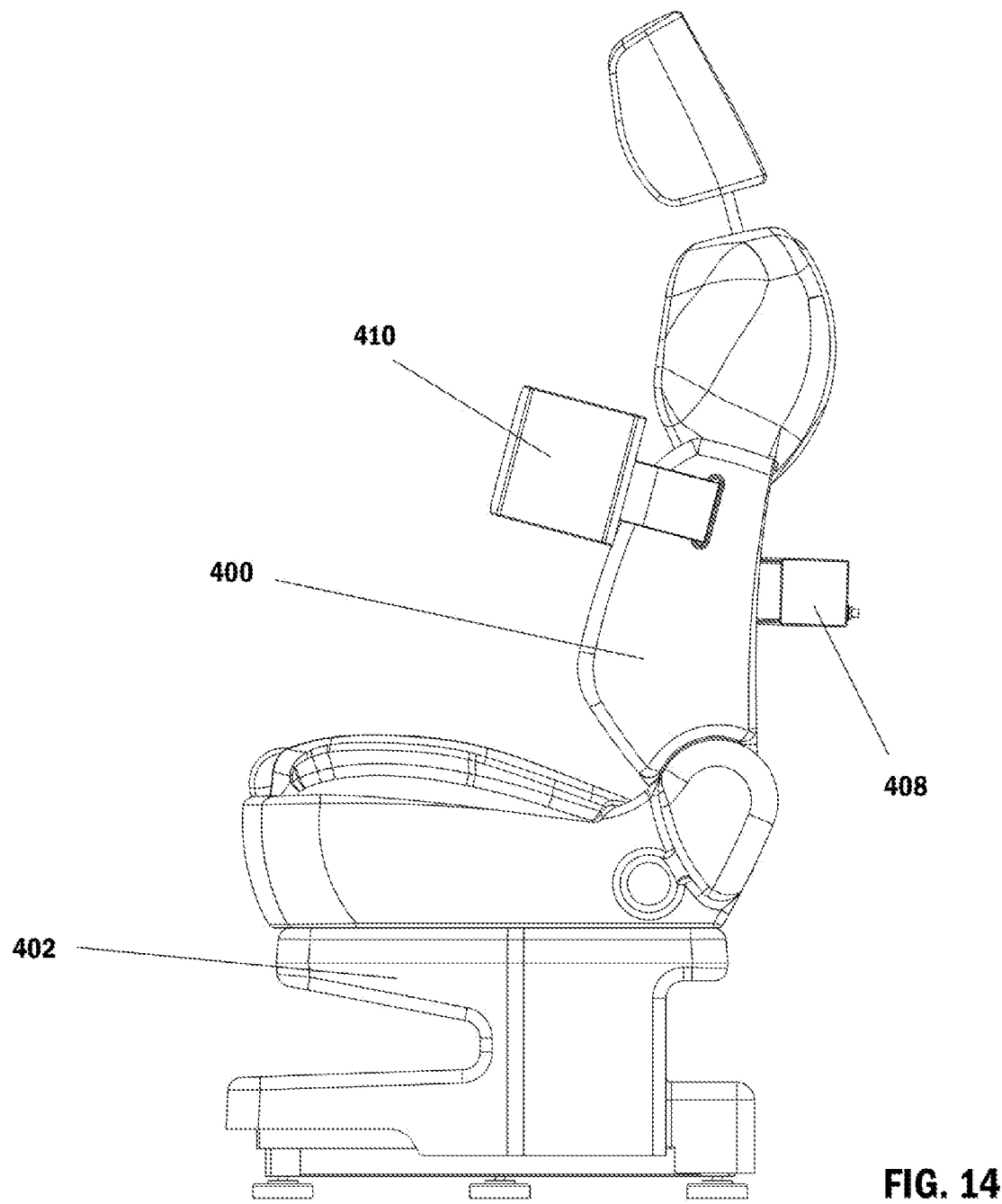
FIG. 14 illustrates a left side elevation view of a multi-sensor seat of a multi-sensor interactive patient care pod, as contemplated by the present disclosure.
Figure 15:
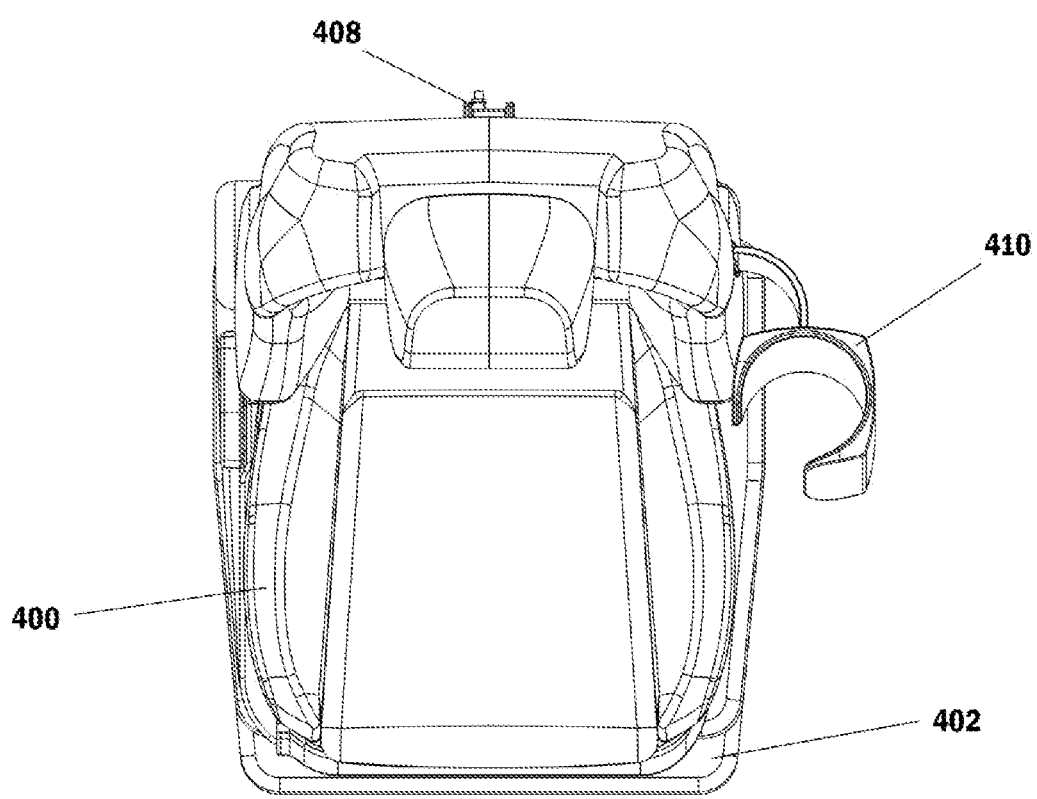
FIG. 15 illustrates a top plan view of a multi-sensor seat of a multi-sensor interactive patient care pod, as contemplated by the present disclosure.
Figure 16:
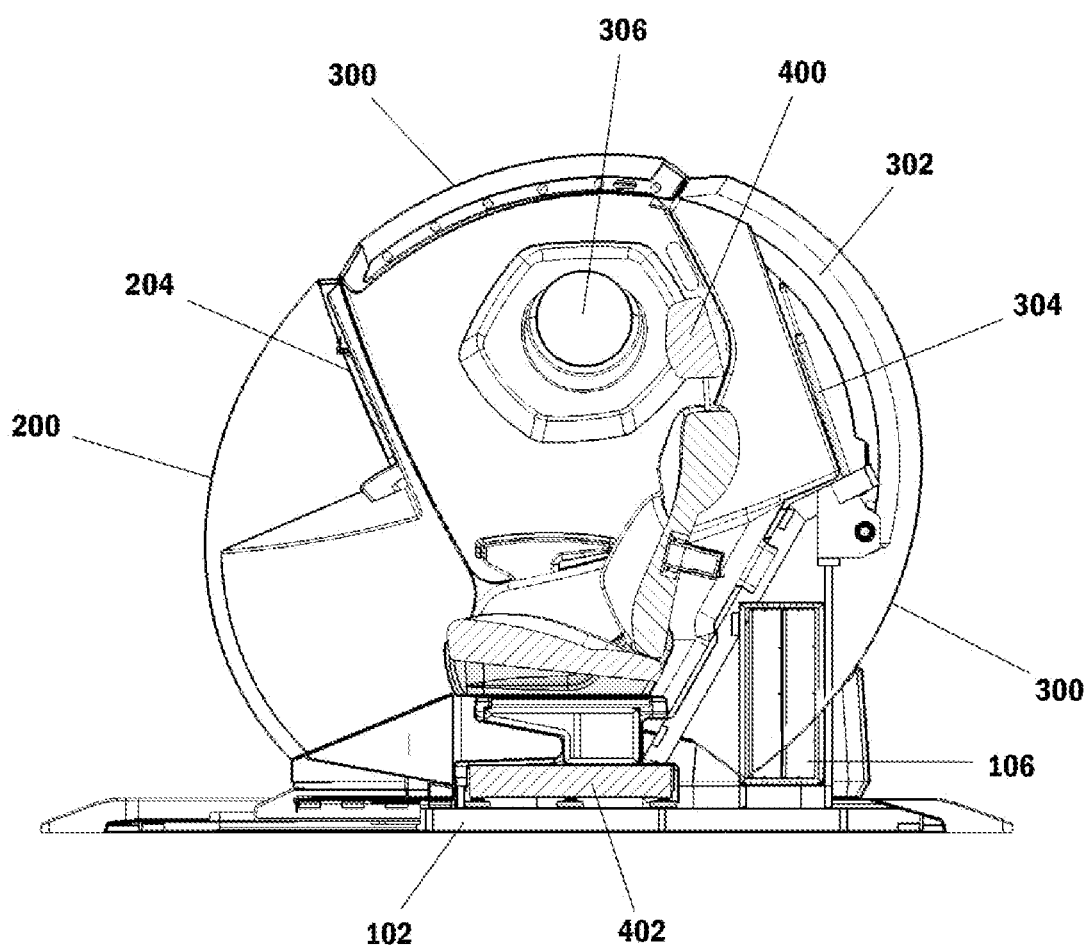
FIG. 16 illustrates a left side cross-sectional view of a multi-sensor seat of a multi-sensor interactive patient care pod, as contemplated by the present disclosure.
Figure 17:
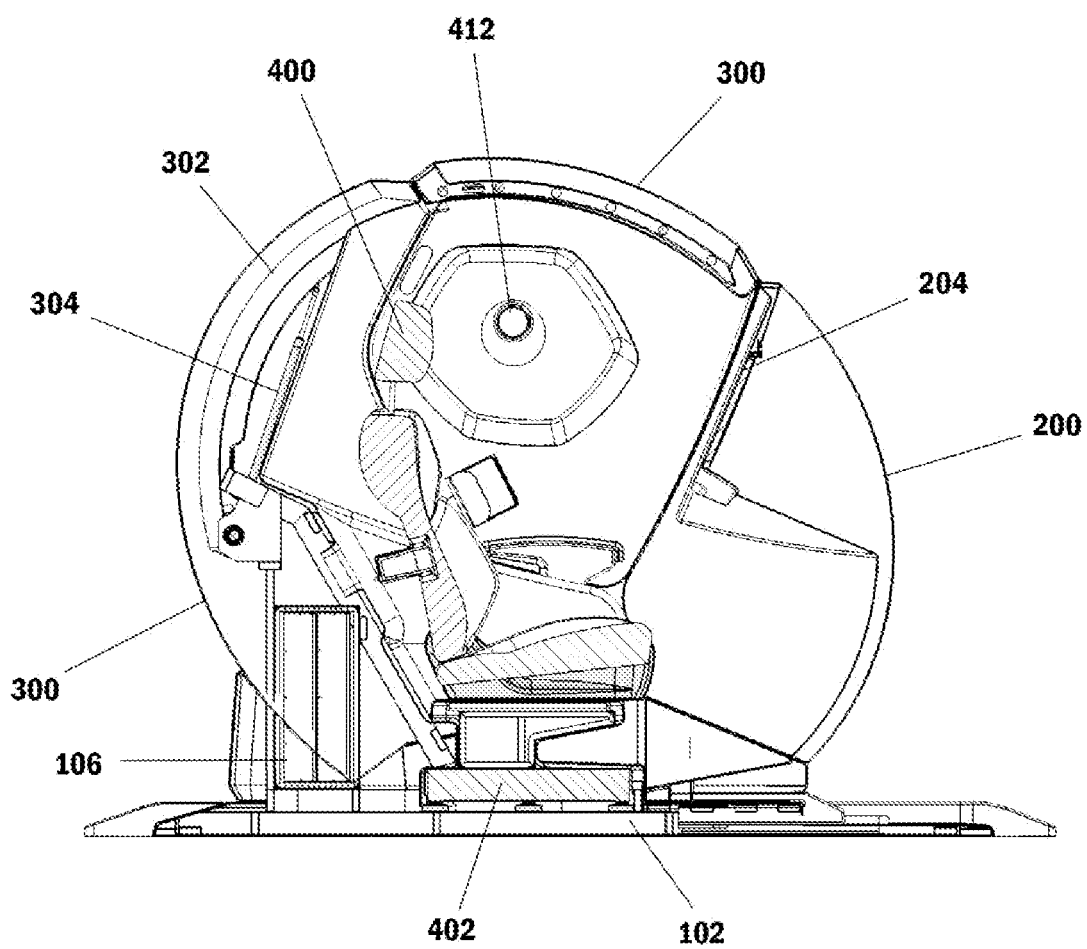
FIG. 17 illustrates a right side cross-sectional view of a multi-sensor seat of a multi-sensor interactive patient care pod, as contemplated by the present disclosure.

Certain terminology is used in the following description for reference only and is not limiting. The words "front," "rear," "anterior," "posterior," "lateral," "medial," "upper," "lower," "outer," "inner," and "interior" refer to directions toward and away from, respectively, the geometric center of the invention, and designated parts thereof, in accordance with the present disclosure. Unless specifically set forth herein, the terms "a," "an," and "the" are not limited to one element, but instead should be read as meaning "at least one." The terminology includes the words noted above, derivatives thereof, and words of similar import.

The illustrations of FIGS. 1-18 illustrate a multi-sensor interactive patient care pod, as contemplated by the present disclosure. In one embodiment the system may comprise a telemedicine pod having a plurality of physiological sensors and an integrated computing device allowing medical practitioners to remotely gather increased patient information and provide advanced levels of healthcare and service. The system may have sensors for measuring body weight, pulse oximetry, body temperature, blood pressure, breathing rate, oxygen saturation, and any other appropriate parameters. The multi-sensor interactive patient care pod may comprise an enclosed pod in a first orientation, and may open by the combined sliding of its front cowling and lifting of its top cowling to allow patient ingress and egress. The system may further comprise a mobile device that can be placed in any appropriate location, and may further integrate smart technologies such as machine learning, voice and face recognition, self-cleaning, self-driving, and self-locking technologies.

The illustrations of FIGS. 1-6 illustrate a multi-sensor interactive patient care pod in a closed orientation, as contemplated by the present disclosure. The system may comprise, generally, a fixed rear cowling 100 attached to a base 102. The rear cowling 100 and base 102 may further comprise a skeletal frame appropriately shaped to maintain the structural composition of the system and support various additional components of the system. The base 102 may comprise a substantially flat shape integrating a track 104, and the rear cowling 100 may comprise a substantially hemispherical shape into which various components of the system may be installed.

The multi-sensor interactive patient care pod may further comprise a front cowling 200 attached to a sled 202. The front cowling 200 may further comprise a skeletal frame appropriately shaped to maintain the structural composition of the front cowling 200 and support various additional components of the system. The sled 202 may be installed within the track 104 of the base 102, and may be motorized or otherwise moved from one end to the other within or along the track 104. The sled 202 may be attached to a lower edge or bottom surface of the front cowling 200 such that the movement of the sled 202 within or along the track 104 also moved the front cowling 200.

The multi-sensor interactive patient care pod may further comprise a top cowling 300 attached to distal ends of a plurality of cowling arms 302. The top cowling 300 may further comprise a skeletal frame appropriately shaped to maintain the structural composition of the top cowling 300 and support various additional components of the system. The plurality of cowling arms 302 may further comprise proximal ends that may be attached to the skeletal frame of the rear cowling 100 or base 102.

The various cowling components of the multi-sensor interactive patient care pod may be oriented relative to each other such that they form an enclosed pod in a closed orientation. By way of example, the rear cowling 100 may be affixed to the base 102 and shaped so as to form a rear one-third of the enclosed pod. The front cowling 200 may be positioned in front of the rear cowling 100 and may able to slide forward and backward over the base 102 relative to the rear cowling 100, and may be shaped so as to form a front one-third of the enclosed pod. The top cowling 300 may be positioned above the rear cowling 100 and the front cowling 200 and may be able to lift upwards and lower downwards along an arc defined by the plurality of cowling arms 302, and may be shaped so as to form a top one-third of the enclosed pod.

The multi-sensor interactive patient care pod may transition from a closed orientation to an open orientation by the simultaneous sliding forward of the front cowling 200 and lifting of the top cowling 300. The multi-sensor interactive patient care pod may transition from an open orientation to a closed orientation by the simultaneous sliding backwards of the front cowling 200 and lowering of the top cowling 300. The open orientation of the multi-sensor interactive patient care pod may permit an individual's ingress and egress relative to the system.

The illustrations of FIGS. 7-17 illustrate an exemplary multi-sensor interactive patient care pod in detail, as contemplated by the present disclosure. The rear cowling 100, base 102, front cowling 200, and top cowling 300 may enclose and support the various components of the system. Components installed within the rear cowling 100 may comprise, generally, a seat 400, a plurality of physiological sensors, and a computing system 106. Components installed within the front cowling 200 may comprise, generally, a display device 204 and a plurality of input and output devices. Components installed within the top cowling 300 may comprise, generally, a plurality of physiological sensors and ambient lighting 308. In various embodiments the various components of the system may be installed in alternate cowlings, as desired.

In one embodiment the rear cowling 100 may enclose a computing device 106 that may perform as a server node for the system, and which may integrate wireless connectivity, a power supply, and environment controls. The wireless connectivity may permit the computing system 106 to communicate with a central server or remote server node to effect the purpose of the system, and may allow communication via radio signal, digital signal, or any other appropriate means. The power supply may be a rechargeable or replaceable onboard battery or may be a plug in connection that supplies power to the system. The environment controls may be any system appropriate for maintaining the temperature, humidity, and cleanliness of the environment within the system.

In one embodiment the front cowling 200 may enclose a display device 204, which may be any appropriate digital display or interactive display, such as a high definition liquid crystal display or a touch screen. A plurality of input devices may also be enclosed within the front cowling 200 allowing a user to interact with the display device 204 or the system. Such plurality of input devices may comprise, for example, a keyboard and mouse combination, a microphone, a facial recognition or gesture recognition camera, or any other appropriate input. The front cowling 200 may further enclose a plurality of speakers for audio output.

In one embodiment the top cowling 300 may enclose a parabolic mirror 306, ambient lighting 308, and a breathing rate sensor 412. The parabolic mirror 306 may allow a wider view of a user of the system by a medical practitioner interacting with that user and may also give an impression that the user is sitting in a larger area to ward off feelings of claustrophobia. The ambient lighting 308 may light up the interior of the system so that a user of the system may visualize the components around them. The breathing rate sensor 412 may be any sensor appropriate for measuring the breathing rate and oxygen saturation of a user of the system. By way of example, the breathing rate sensor 412 may comprise a flow visualization sensor, which may be known as a Schlieren device, to measure gas vapors emanating from the user. Oxygen saturation may be calculated by the computing device 106 based on the partial pressure of oxygen measured by the sensors of the system.

In one embodiment the seat 400 may comprise a seat base 402 and a plurality of armrests 404 housing a plurality of physiological sensors. The seat base 402, for example, may enclose a body weight sensor, which may be resistance scale sensor for measuring the weight of a user sitting within the seat. One of the plurality of armrests 404, for example, may enclose a pulse oximetry sensor 406, which may be spectrally-paired photo detectors for measuring the pulse oximetry of the user. The back panel of the seat 400 may enclose a body temperature sensor 408, which may be short range microwave radiometry sensors for measuring the heat radiating from a user. The back panel of the seat 400 may also be attached to a blood pressure sensor 410, which may be a blood pressure cuff into which the user may place their arm for taking blood pressure readings.

In one embodiment the multi-sensor interactive patient care pod may further comprise a red light therapy device, which may be, for example, a plurality of light-emitting diodes (LEDs) emitting light in the 660 nanometer (nm) range built into the top cowling 300 or integrated into the ambient lighting 308.

In one embodiment the lifting and lowering of the top cowling 300 may be supported or augmented by any appropriate means. By way of example, the system may further comprise a plurality of cowling supports 304, which may comprise lift shocks, attached to the various frames of the system.

In one embodiment the multi-sensor interactive patient care pod may further comprise a self-cleaning technology, which may be, for example, an ultra-violet (UV) sterilization device. The self-cleaning technology could, alternatively, comprise a disinfectant container and a plurality of sprayer nozzles for pressure washing or spraying down the system.

In one embodiment the multi-sensor interactive patient care pod may further comprise a non-slip surface applied over the base 102 to provide a user with additional traction and reduce the likelihood of an accidental slip and fall from the system.

In one embodiment the multi-sensor interactive patient care pod may further comprise a proprietary software, which may be used to reserve or operate the system. The proprietary software application may be integrated for appointments of the system, accessing the system, and controlling the system during use.

In one embodiment the multi-sensor interactive patient care pod may further comprise an access interface and a pod lock. The pod lock may be an automated device with electronically controlled functions over an internet-enabled cloud application or via near-field communication (NFC) technology authenticated via biometric sensing. In another embodiment, the pod lock may be a magnetic lock unlocked and locked by a pre-assigned passcode. In any embodiment the activation of the pod lock may be controlled by a user's interaction with the access interface, such as, for example, by logging in to a user account via the access interface or by scanning a code displayed on a mobile phone via the access interface.

In one embodiment the wireless connectivity may be a wireless access point using wireless fidelity (Wi-Fi) technology with a backhaul provided by a wireline ethernet network, or the internet connectivity device may be a wireless cellular network with a localized wireless access point providing a network hotspot. The Wi-Fi technology may be used to connect the multi-sensor interactive patient care pod to a central server and the internet. Wi-Fi access by a user of the system may be permitted during their appointment.

The multi-sensor interactive patient care pod may further comprise a plurality of cameras used for image processing. The processed images may be analyzed using machine learning to determine if the system is occupied by users at unexpected times, is occupied by an unexpected number of users, is left dirty or requires cleanup or maintenance, or if a person using the system has left behind personal items. The system may detect such anomalies and react, as appropriate, by notifying a central database, notifying a cleaning or maintenance crew, or notifying the previous user of the multi-sensor interactive patient care pod.

Inputs to the multi-sensor interactive patient care pod user interface may be made by any appropriate means such as, for example, text-based input or voice-based input. In an embodiment comprising text-based input, the user may type queries and commands into the user interface using any appropriate input source, such as a physical or virtual keyboard or a smartphone or tablet device connected to the system, whether physically or wirelessly. In an embodiment comprising voice-based input the user may interact with the system using a microphone, whether individually or integrated into a smartphone or tablet device, and the system may comprise speech recognition and language interpretation components to understand and interpret the input.

To protect the various user accounts, user data, and transactions stored within the system it is contemplated that the proprietary software may implement modern data security and encryption protocols. By way of example, the proprietary software may implement the advanced encryption standard (AES), the triple data encryption standard (3DES), the twofish standard, the Rivest, Shamir, Adelman standard (RSA), or any other appropriate encryption protocol. It is contemplated that the proprietary software may implement, at least, 128-bit encryption, though more difficult encryption, such as, for example, 206-bit or 256-bit, may be implemented as desired.

The multi-sensor interactive patient care pod may be substantially constructed of any suitable material or combination of materials, but typically is constructed of a resilient material or combination of materials such that the device is resistant to damage as a result of compression, twisting, heating, or submersion in water. As an example, and without limiting the scope of the present invention, various exemplary embodiments of the multi-sensor interactive patient care pod may be substantially constructed of one or more materials of plastic, acrylic, polycarbonate, steel, aluminum, brass, fiberglass, carbon fiber, or combinations thereof. In some embodiments the various components of the system may be coated, lined, or otherwise insulated to prevent contamination. In one embodiment the material of construction may vary from one component to the next within the system.

In one embodiment the multi-sensor interactive patient care pod may comprise a resilient material of construction that either comprises a material having antimicrobial properties or comprises a layering of antimicrobial material or coating. Antimicrobial properties comprise the characteristic of being antibacterial, biocidal, microbicidal, anti-fungal, anti-viral, or other similar characteristics, and the oligodynamic effect, which is possessed by copper, brass, silver, gold, and several other metals and alloys, is one such characteristic. Copper and its alloys, in particular, have exceptional self-sanitizing effects. Silver also has this effect, and is less toxic to users than copper. Some materials, such as silver in its metallic form, may require the presence of moisture to activate the antimicrobial properties.

In one embodiment the multi-sensor interactive patient care pod may comprise a palleted floor having retractable wheels and stands. In this way the system may be moved on its own wheels by pushing or pulling, or may be lifted by a forklift or similar device, or may be moved and positioned by using a pallet jack.

In a self-driving embodiment, the multi-sensor interactive patient care pod may comprise any combination of autonomous components and automobile components, though most relevant to the invention are its powertrain, suspension, and braking subsystems. The autonomous system controls these various subsystems via actuation means that may accelerate, turn, and brake the system under its direction. To determine the appropriateness of such controls, the autonomous system further comprises a plurality of sensors that allow for detection of the surrounding area and the present state of the system. In one embodiment the autonomous system further comprises a database of route maps and known traffic rules and behaviors acceptable to its operating environment.

In one embodiment the multi-sensor interactive patient care pod may allow a user to make payments to the system using any appropriate payment method, such as STRIPE, SQUARE, PAYPAL, GOOGLE PAY, or APPLE PAY.

Figure 18:
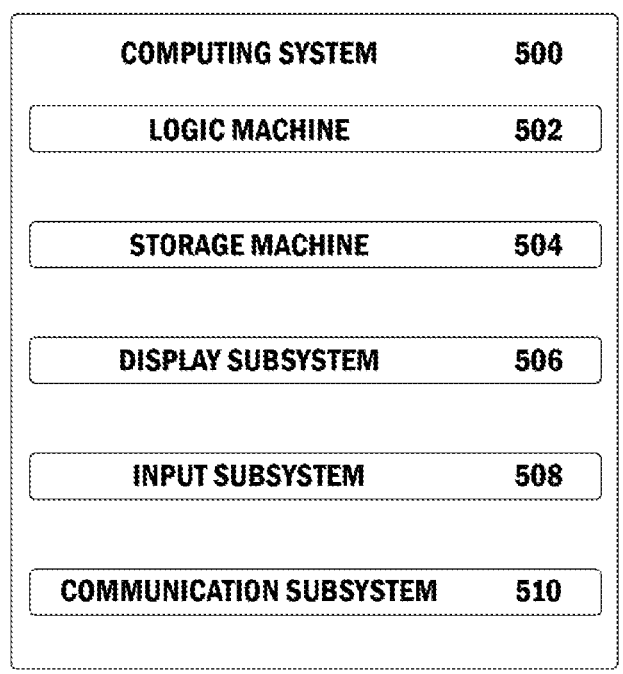
FIG. 18 schematically presents a computing system configured to carry out and actualize methods and tasks described herein, as contemplated by the present disclosure.

The illustration of FIG. 18 schematically presents a computing system configured to carry out and actualize methods and tasks described herein. In some embodiments the method is executed on a computing system such as computing system 500. For example, storage machine 504 may hold instructions executable by logic machine 502 to provide the method to users.

Display subsystem 506 may display the various elements of the method to participants. For example, display subsystem 506, storage machine 504, and logic machine 502 may be integrated such that the method may be executed while being displayed on a display screen. The input subsystem 508 may receive user input from participants to indicate the various choices or user inputs described above.

The described method may be executed, provided, or implemented to a user on one or more computing devices via a computer-program product such as via an application programming interface (API). Computing system 500 may be any appropriate computing device such as a personal computer, tablet computing device, gaming device or console, mobile computing device, etc. Computing system 500 includes a logic machine 502 and a storage machine 504. Computing system 500 may include a display subsystem 506, input subsystem 508, and communication subsystem 510.

Logic machine 502 may execute machine-readable instructions via one or more physical devices. For example, the logic machine 502 may be configured to execute instructions to perform tasks for a computer program. The logic machine may include one or more processors to execute machine-readable instructions.

Storage machine 504 includes one or more physical devices configured to hold or store instructions executable by the logic machine to implement the method. When such methods and processes are implemented, the state of storage machine 504 may be changed to hold different data. For example, storage machine 504 may include memory devices such as various hard disk drives or CD or DVD devices.

Display subsystem 506 may visually present data stored on storage machine 504. For example, display subsystem 506 may visually present data to form a graphical user interface (GUI). Input subsystem 508 may be configured to connect and receive input from devices such as a mouse, keyboard, or gaming controller. Communication subsystem 510 may be configured to enable system 500 to communicate with other computing devices. Communication subsystem 510 may include wired and/or wireless communication devices to facilitate networked communication.

While the invention has been described in connection with what is presently considered to be the most practical and preferred embodiments, it is to be understood that the invention is not to be limited to the disclosed embodiments, but, on the contrary, is intended to cover various modifications and equivalent arrangements included within the spirit and scope of the appended claims.

I claim:

1. A multi-sensor interactive patient care pod, comprising:
a base;
a rear cowling;
a front cowling;
a top cowling;
a seat; and
a plurality of physiological sensors;
wherein said base further comprises a track and a skeletal frame;
wherein said rear cowling is fixedly attached to said base;
wherein said front cowling further comprises a sled;
wherein said sled of said front cowling is attached to said track of said base;
wherein said top cowling further comprises a plurality of cowling arms;
wherein said plurality of cowling arms of said top cowling are attached to said skeletal frame of said base;
wherein said seat is attached to said base within said rear cowling; and
wherein said rear cowling, said front cowling, and said top cowling abut one another to form an enclosed pod in a closed orientation.

2. The patient care pod of claim 1,
wherein said front cowling is reversibly moved forward by said sled;
wherein said top cowling is reversibly moved upward by said plurality of cowling arms; and
wherein said front cowling and said top cowling are moved away from said rear cowling to form an open pod in an open orientation.

3. The patient care pod of claim 2, further comprising:
a computing device; and
a proprietary software;
a wireless connectivity;
wherein said computing device is attached to said skeletal frame of said base;
wherein said proprietary software is accessed via said computing device;
wherein said proprietary software sends a plurality of instructions to said plurality of physiological sensors;
wherein said proprietary software receives a plurality of data from said plurality of physiological sensors; and
wherein said wireless connectivity allows said computing device and said proprietary software to connect wirelessly to a central server.

4. The patient care pod of claim 3,
wherein one of said plurality of physiological sensors comprises a pulse oximetry sensor.

5. The patient care pod of claim 4,
wherein one of said plurality of physiological sensors comprises a body temperature sensor.

6. The patient care pod of claim 5,
wherein one of said plurality of physiological sensors comprises a blood pressure sensor.

7. The patient care pod of claim 6,
wherein one of said plurality of physiological sensors comprises a breathing rate sensor.

8. The patient care pod of claim 7,
wherein one of said plurality of physiological sensors comprises an oxygen saturation sensor.

9. The patient care pod of claim 8, further comprising:
a plurality of displays;
wherein said plurality of displays are controlled by said proprietary software.

10. The patient care pod of claim 9, further comprising:
a plurality of input devices;
wherein said plurality of input devices allow a user to interact with said computing device.

11. The patient care pod of claim 10, further comprising:
a plurality of speakers;
wherein said plurality of speakers are controlled by said proprietary software; and
wherein said plurality of speakers output audio within said enclosed pod.

12. The patient care pod of claim 11, further comprising:
a plurality of lights;
wherein said plurality of lights are controlled by said proprietary software; and
wherein said plurality of lights output light within said enclosed pod.

13. The patient care pod of claim 12, further comprising:
an air conditioning system;
wherein said air conditioning system is controlled by said proprietary software; and
wherein said air conditioning system modifies an environment within said enclosed pod.

14. The patient care pod of claim 13, further comprising:
a plurality of cameras;
wherein said plurality of cameras are controlled by said proprietary software; and
wherein said plurality of cameras monitor conditions within said enclosed pod.

15. The patient care pod of claim 14, further comprising:
a parabolic mirror.

16. The patient care pod of claim 15, further comprising:
a red light therapy device.

17. The patient care pod of claim 16, further comprising:
an antimicrobial material of construction.

18. The patient care pod of claim 17,
a self-cleaning technology.

19. The patient care pod of claim 18, further comprising:
a plurality of wheels;
wherein said plurality of wheels are attached to said base;
wherein said plurality of wheels allow said enclosed pod to be rolled; and
wherein said plurality of wheels are reversibly lockable.

20. The patient care pod of claim 19, further comprising:
a self-driving technology.

* * * * *